United States Patent [19]

Glazier

[11] Patent Number: 5,659,061

[45] Date of Patent: Aug. 19, 1997

[54] TUMOR PROTEASE ACTIVATED PRODRUGS OF PHOSPHORAMIDE MUSTARD ANALOGS WITH TOXIFICATION AND DETOXIFICATION FUNCTIONALITIES

[75] Inventor: Arnold Glazier, Newton, Mass.

[73] Assignee: Drug Innovation & Design, Inc., Newton, Mass.

[21] Appl. No.: 425,477

[22] Filed: Apr. 20, 1995

[51] Int. Cl.$^6$ .................................. C07F 9/02; A61K 31/66
[52] U.S. Cl. ...................... 558/166; 558/169; 558/170; 558/171; 514/114; 514/118; 514/137; 514/553; 514/603; 562/67; 564/85; 564/94
[58] Field of Search .......................... 558/166, 169, 558/170, 171, 172; 514/118, 553, 603, 114, 137; 562/67; 564/85, 94

[56] References Cited

U.S. PATENT DOCUMENTS 5,274,162  12/1993  Glazier ..................................... 558/553

FOREIGN PATENT DOCUMENTS 43 09 344    9/1994   Germany .
WO89/11484  11/1989   WIPO .

Primary Examiner—John W. Rollins
Attorney, Agent, or Firm—Hamilton, Brook, Smith & Reynolds, P.C.

[57] ABSTRACT

The composition, synthesis, and applications of tumor associated protease activated prodrugs of phosphoramide mustard, isophosphoramide mustard and analogs with detoxification functionalities are described. These drugs release a cytotoxic phosphoramide mustard analog following activation by tumor associated proteases and esterases. The general structure for these drugs is:

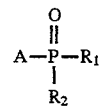

Wherein R1 is a beta-X-ethyl-amino group which may optionally bear substituents on the nitrogen or carbon atoms; wherein X is a good leaving group such as a halogen; R2 is a beta-X-ethyl-amino group which may optionally bear substituents on the nitrogen or carbon atoms; or an amino group ($NH_2$) which may optionally be substituted. Wherein A is a benzyloxy derivative with one or more acyloxy or acylamino groups in para or ortho portions relative to the phosphoester; and wherein the acyloxy or acylamino groups are not (substituted or unsubstituted) p-guanidino-benzoyloxy groups or p-guanidino-benzoylamino groups.

25 Claims, 3 Drawing Sheets

ANTITUMOR ACTIVITY AND BONE MARROW TOXICITY OF V-ISOPHOS

FRACTION OF SURVIVING CELLS

V-ISOPHOS

| Drug Dose mg/kg | Tumor | Marrow CFU-GM |
|---|---|---|
| 0 | 1 | 1 |
| 50 | 0.69 | 0.60 |
| 100 | 0.19 | 0.44 |
| 150 | 0.08 | 0.40 |
| 200 | .067 | 0.36 |

IFOSFAMIDE

| Drug Dose mg/kg | Tumor | Marrow CFU-GM |
|---|---|---|
| 0 | 1 | 1 |
| 100 | 0.20 | 0.42 |
| 300 | 0.07 | 0.077 |
| 500 | .0018 | 0.026 |

CYTOXAN

| Drug Dose mg/kg | Tumor | Marrow CFU-GM |
|---|---|---|
| 0 | 1 | 1 |
| 100 | 0.138 | 0.26 |
| 300 | 0.14 | 0.038 |
| 500 | .00035 | 0.0059 |

4-HYDROPEROXY CYCLOPHOSPHAMIDE

| Drug Dose mg/kg | Tumor | Marrow CFU-GM |
|---|---|---|
| 0 | 1 | 1 |
| 100 | 0.092 | 0.44 |
| 150 | 0.083 | 0.18 |
| 200 | 0.061 | 0.12 |
| 300 | 0.0032 | 0.07 |
| 400 | 0.00024 | 0.026 |

TUMOR PROTEASE ACTIVATED PRODRUGS OF PHOSPHORAMIDE MUSTARD ANALOGS WITH TOXIFICATION AND DETOXIFICATION FUNCTIONALITIES

TECHNICAL FIELD

This invention is in the fields of chemistry, medicine and pharmacology.

BACKGROUND

Despite the major advances in clinical cancer therapy due to alkylating agents, drugs of this class have severe limitations. The major problem is one of nonspecific toxicity. There have been numerous attempts to develop alkylating agents which are selectively targeted to tumor cells. With few exceptions the results have been uniformly discouraging. For example, alkylating agents which are activated by .enzymes present in tumor tissue such as alkaline phosphatase, azo-reductase, glucuronidase, plasmin, and collagenase have been explored.
Ross, W. C.; Warwick, G. P.; Roberts J. J.; *J. Chem. Soc.* 3100 (1955). Connors, T. A.; Foster, A. B., Tisdale, M. J.; (1972) *Biochem. Pharmacol.* 21:1309. Connors, T. A.; Whisson, M. E.; (1966) *Nature* 210:866; Ball, C. R.; Double, J. A.; (1974) *Biochem. Pharmacol.* 23:3173.; Workman, P.; Double, J. A.; (1977) *Biochem. Pharmacol.* 27:199.; Marquissee, M. J.; Kauer, J. C. (1978); *J. Med. Chem.* 21:1188; Chakravarty, P.; Carl, P.; Weber, M.; Katzenenellenbogen, J.; (1983); *J. Med. Chem.;* 26:633; and 26:638

The fundamental problem remains one of tumor specificity. Although the tumor may have many fold higher levels of the target enzyme normal tissues also invariably possess some of the enzyme which ultimately activates the alkylating agent and results in toxicity. This severely limits tumor selectivity.

In order to circumvent these problems a new class of tumor selective antineoplastic agents was developed. *Antineoplastic Drugs with Bipolar Toxification/Detoxification Functionalitites*, A. Glazier, (1993) U.S. Pat. No. 5,274,162. These novel antineoplastic agents have two key functionalities: a trigger which toxifies the drug; and an deactivator which detoxifies the drug. The trigger is selected such that it is activated by an enzyme which is present in elevated levels in the tumor. The deactivator is selected such that it is actuated by an enzyme ubiquitous to all tissues. The fate of the drug in a given cell is then determined by the ratio of the enzymatic activity that triggers toxication to the enzymatic activity which detoxifies the drug. The partitioning of the drug between toxic metabolite and nontoxic metabolite defines the resulting specificity of cytotoxic effect. U.S. Pat. No. 5,274,162. by A. Glazier describes a new class of antineoplastic drugs designed to be selectively toxic for tumor cells bearing the enzyme guanidinobenzoatase.

A fundamental characteristic of malignant cells is tissue invasiveness. In order for malignant cells to multiply and spread the cells must degrade the extracellular matrix. An extensive body of scientific data exists which details the crucial role of tumor associated proteases in the processes of malignancy. Tumor associated enzymes implicated in the degradation of the tumor extracellular matrix include: urokinase; tissue plasminogen activator, Cathepsin B; Cathepsin C; Cathepsin D; plasmin; collagenase; Type IV collagenase; and stromelysin.
Liotta L; *Cancer Metastasis Rev* (1990) 9(4):285–7 Kwaan H C; *Cancer Metastasis Rev* (1992) 11(3–4):291–311 Testa J E Quigley J P; *Cancer Metastasis Rev* (1990) 9(4):353–67 Sloane B F Moin K Krepela E Rozhin J; *Cancer Metastasis Rev* (1990) 9(4):333. Rochefort H Capony F Garcia M; *Cancer Metastasis Rev* (1990) 9(4):321. McDonnell S Matrisian L M; *Cancer Metastasis Rev* (1990) 9(4):305. Stetler-Stevenson W G; *Cancer Metastasis Rev* (1990) 9(4:289 Matrisian L M McDonnell S Miller D B Navre M Seftor E A Hendrix M J; *Am J Med Sci* (1991) 302(3): 157–62; Sukoh N Abe S Ogura S Isobe H Takekawa H Inoue K Kawakami Y; *Cancer* (1994) 74(1):46–51; Kobayashi H Ohi H Sugimura M Shinohara H Fujii T Terao T; *Cancer Res* (1992) 52(13):3610–4 Mulcahy H E Duffy M J Gibbons D McCarthy P Parfrey N A O'Donoghue D P Sheahan; K; *Lancet* (1994) 344(8922):583

Substantial effort has been directed towards the development of inhibitors to these tumor associated proteases as potential anticancer drugs to slow tumor invasion and growth. DeClerck Y A; Imren S; *Eur J Cancer* (1994) 30A(14): 2170–80. However, inhibitors to tumor associated proteases are not lethal to tumor cells and at best would be expected to only slow tumor growth.

SUMMARY OF THE INVENTION

This invention relates to a new class of tumor selective antineoplastic agents which release a cytotoxic phosphoramide mustard analog following activation by tumor associated proteases and esterases. The general structure for the class of tumor associated protease selective antineoplastic drugs is Formula 1:

Wherein R1 is a beta-X-ethyl-amino group which may optionally bear substituents on the nitrogen or carbon atoms; wherein X is a good leaving group such as a halogen; R2 is a beta-X-ethyl-amino group which may optionally bear substituents on the nitrogen or carbon atoms; or an amino group ($NH_2$) which may optionally be substituted. Wherein A is a benzyloxy derivative with one or more acyloxy or acylamino groups in para or ortho positions relative to the phosphoester; and wherein the acyloxy or acylamino groups are not (substituted or unsubstituted) p-guanidino-benzoyloxy groups or p-guanidino-benzoylamino groups.

DETAILED DESCRIPTION OF THE INVENTION

General Structure

The present class of antineoplastic drugs are designed such that the enzymatic activity of tumor associated protease triggers the production of a potent bifunctional alkylating agent. This alkylating agent then kills the tumor cells by cross linking DNA or by inactivating vital enzymes. The tumor associated protease triggers the activation and release of a phosphoramide type mustard derivative by cleaving an appropriately located amide of ester functionality. Activated phosphoramide mustard derivatives are the toxic species which mediated the anticancer effects of cyclophosphamide and iphosphamide. Freidman, O.; Myles, M.; Colvin, M. (1979) *Advances in Cancer Chemotherapy;* 1:143. Boyd, V.; Robbins, J.; Egan, W.; Ludeman, S.; (1986); *J. Med. Chem.;* 29:1206 Compounds such as cyclophosphamide, ifosfamide, and benzylic esters of phosphoramide mustard are not active alkylating agents. In the absence of biotransformation these compounds are relatively nontoxic. The electron withdrawing influence of the phosphorus atom dramatically depresses the ability of the adjacent nitrogen to attack the chloro-ethyl group and produce an aziridinium cation. However, conversion of the phospho-ester group of compounds such as cyclophosphamide, ifosfoamide, and esters of phosphoramide mustard to a negatively charged species enormously increases the nucleophilicity of the adjacent nitrogen. This triggers the formation of the highly toxic aziridinium cation. Brock, N. (1976); *Cancer Treatment Rep.;* 60:301. Kwon, C.; Moon, K.; Baturay, N.; Shirota, F.; (1991); *J. Med. Chem.;* 34:588.

Tumor associated proteases and esterases which may activate the present class of anticancer drugs include but are not limited to: urokinase; tissue plasminogen activator, Cathepsins; Cathepsin B; Cathepsin L; Cathepsin C; Cathepsin D; plasmin; collagenase; Type IV collagenase; stromelysin; and dipeptidyl peptidase.

A subset of the present class of antineoplastic drug consist of two key functionalities: a trigger which toxifies the drug; and an deactivator which detoxifies the drug. The trigger is selected such that it is activated by a tumor associated protease which is present in elevated levels in the tumor. The deactivator is selected such that it is actuated by an enzyme ubiquitous to all tissues. The fate of the drug in a given cell is then determined by the ratio of the enzymatic activity that triggers toxication to the enzymatic activity which detoxifies the drug. The partitioning of the drug between toxic metabolite and nontoxic metabolite defines the resulting specificity of cytotoxic effect. In normal tissues with low levels of the triggering enzyme the drug is largely detoxified. In tumor cells with high levels of the triggering enzyme a high percentage of the drug is activated to a cytotoxin. Oncospecificity is further enhanced by selection of a toxic species which itself also has preferential toxicity for malignant cells. The deactivator functionality may also be designed such that it is actuated independently of enzymes in a spontaneous fashion. In this case the deactivator serves as an internal clock. Oncospecificity results directly from quantitative differences in the levels of triggering enzyme in tumor versus normal tissues.

A number of enzymes may be selected to actuate the detoxification of these selective antineoplastic drugs. The key requirement is that the enzyme selected should be present in normal tissues and capable of detoxifying the phosphoramide mustard. In the preferred embodiment of the detoxification mechanism a nucleophile is unmasked by the detoxifying enzyme and reacts intramolecularly with the aziridinium cation. This will preclude the alkylation of DNA and vital cellular enzymes. In the preferred embodiments of the detoxification mechanism the detoxifying enzyme unmasks a nucleophile which is positioned such that it will react intramolecularly to form a 4, 5, or 6 membered ring and concomitantly inactivate the ability of the compound to be a bi-functional alkylating agent. The masked nucleophile (Nu) may be any group such as a hydroxy, thiol, amine, or carboxylate moiety. A key requirement is that the nucleophile should be unmasked by an enzyme which is ubiquitous to normal tissues but not by the tumor selective toxifying enzyme. For example, hydroxy groups and carboxylate groups can be masked as esters which may be cleaved by ubiquitous nonspecific esterase. Amino groups can be masked as amides or as azo moieties which can be unmasked respectively by proteases or azoreductases. Thiols can be masked as thio-esters or disulfides. Thiol esters can be cleaved by thiol-esterases. Disulfides can be reduced to thiols by a variety of enzymatic processes. The deactivator functionality may also be selected such that it is activated independently of enzymes. The nucleophile may be masked as a functionality which undergoes spontaneous nonenzymatic transformation to yield the exposed nucleophile. In this case the detoxification mechanism functions as an internal clock. Oncospecificity will result directly from quantitative differences in the levels of triggering enzyme in tumor versus normal tissues. For example, a hydroxy group could be masked as an enol ether. An amino group could be masked as an enamine.

The general structure for the class of tumor associated protease selective antineoplastic drugs Formula 1:

Formula 1

Wherein R1 is a beta-X-ethyl-amino group which may optionally bear substituents on the nitrogen or carbon atoms. Wherein X is a good leaving group such as a halogen.

R2 is a beta-X-ethyl-ago group which may optionally bear substituents on the nitrogen or carbon atoms; or an amino group (NH$_2$) which may optionally be substituted.

Wherein A is a benzyloxy derivative with one or more acyloxy or acylamino groups in para or ortho positions relative to the phosphoester; and wherein the acyloxy or acylamino groups are not (substituted or unsubstituted) p-guanidino-benzoyloxy groups or p-guanidino-benzoylamino groups.

Some preferred embodiments are shown below as Formula 2:

Wherein R3 and R4 is H; an alkyl group; a methyl group; or an ethyl group; —CH$_2$—CO$_2$—Y; or an N substituted methylene-carbonyl-amino group; were Y is an alkyl group; a methyl group; or an ethyl group; and R5 is an acyl-oxy group; or an acyl-amino group; and wherein the benzyl ring may optionally be substituted with inert groups; alkyl group; alkyloxy groups, methoxy, or halogen.

The structures of tumor protease activated anticancer drugs which release isophosphoramide mustard and phosphoramide mustard are shown below as Formula 3a –b Formula 3a Formula 3b In a preferred embodiment the drugs have the structure shown below as Formula 4a–b.

Formula 4a

Formula 4b

The preferred structure for R5 is a group given by the following Formulae 5a–5b;

$$R_6-\overset{O}{\underset{}{\overset{\|}{C}}}-\underset{H}{N}-\text{ or } R_6-\overset{O}{\underset{}{\overset{\|}{C}}}-O-$$

Formula 5a    Formula 5b

Wherein R6 is a substituted or unsubstituted alkyl or phenyl group; or wherein R6 is selected such that R6—COOH is a substituted or unsubstituted amino acid or an oligopeptide comprised of from 2 to about 20 substituted or unsubstituted amino acids.

The general structure for the class of tumor protease activated antineoplastic drugs which have a detoxification functionality is given by Formula 6:

Wherein A is a benzyloxy derivative with one or more acyloxy or acylamino groups in para or ortho positions relative to the phosphoester; and wherein the acyloxy or acylamino groups are not (substituted or unsubstituted) p-guanidino-benzoyloxy groups or p-guanidino-benzoylamino groups.

R1 is a beta-X-ethyl-amino group which bears a masked nucleophile substituent on the nitrogen or carbon atoms such that the substituent is located 3, 4, or 5 atoms from the group X.

Wherein X is a good leaving group such as a halogen. Chlorine is the preferred halogen.

R2 is a beta-X-ethyl-amino group which bears a masked nucleophile substituent on the nitrogen or carbon atoms such that the substituent is located 3, 4, or 5 atoms from the group X; or an amino group ($NH_2$) which may optionally be substituted.

Preferred masked nucleophiles include: a hydroxy group; an amino group; a carboxylate group; or a thiol. Preferred groups that mask the nucleophile include: an acyloxy group ($RCO_2$—); an acyl-sulfanyl group (R(CO)—S—) group; or acyl-amino group (R(CO)—NH—). If carboxylate is the nucleophile it is preferably masked as an ester or amide.

The preferred structure for the class of tumor protease activated antineoplastic drugs which have a detoxification functionality is given by Formula 7:

Wherein R3 and R4 is H; alkyl group such as $CH_3$; ethyl; —$CH_2$—$CO_2$—Y, were Y is an alkyl group such as methyl, ethyl; or an N substituted methylene-carbonyl-amino group. The benzyl ring may optionally be substituted with inert groups such as alkyl, methoxy, or halogens.

R5 is an acyl-oxy group; or an acyl-amino group. The preferred structure for R5 is shown below as Formula 8a–b

Formula 8a    Formula 8b wherein R6 is a substituted or unsubstituted alkyl or phenyl group; or wherein R6 is selected such that R6—COOH is a substituted or unsubstituted amino acid or an oligopeptide comprised of from 2 to about 20 substituted or unsubstituted amino acids.

The preferred structures for the class of tumor protease activated antineoplastic drugs which have a detoxification functionality are given by Formula 9a–e:

Formula 9a

Formula 9b

Formula 9c

Formula 9d

Formula 9e

Wherein R7 is O, NH, or S and R8 is an alkyl group, a substituted or unsubstituted phenyl group, or wherein R8—$CO_2H$ is a substituted or unsubstituted amino acid.

Mechanism of Action

Compounds given by Formula 1 will be converted into a potent cytotoxin by the action of tumor associated protease which is present on the surface of tumor cells or in the microenviroment of the tumor. The protease will selectively cleave the acyloxy or acylamino groups in the para or ortho positions of the benzylic ring and liberate at the surface of the tremor cell an unstable intermediate with a para or ortho hydroxy or amino group. This intermediate will rapidly diffuse into and across the tumor cell membrane. The strongly electron donating hydroxy or amino group which is unmasked in turn will trigger the heterolytic cleavage of the benzylic phospho-ester. The net effect will be to generate both intra and extracellularly the species with the key structural elements shown below as Formula 10:

X: good leaving group such as: Cl, 1, Br, F, —$OSO_2CH_3$ which will undergo rapid cyclization to form a highly toxic aziridinium type cation:

This intermediate will then react with DNA and other vital cellular components and kill the to tumor cells. The potent antineoplastic activity of compounds which release intermediates with this structure is well established as exemplified by cyclophosphamide, ifosfamide, and isophosphoramide mustard.

For a detailed discussion of the chemical mechanisms involved in the heterolytic cleavage of the C—O bond to liberate the compound shown as Formula 10 see Australian patent 651835, (1994) *Phosphorous Prodrugs* by A. Glazier. The present drugs are based on and representative of a class of prodrugs for phosphorus compounds in which unmasking of a strongly electron donating substituent in an ortho or para position (such as an amino group) triggers release of the negatively charged phosphorus compound. The rate at which the C—O bond of a compound of Formula 1 undergoes heterolytic cleavage is a function of the Hammett sigma+ constituents on the benzene ring. Electron donating substituents dramatically increase the rate of solvolysis. Cleavage of the ester or amide functionality by protease unmasks respectively a para-hydroxy or p-amino group. These groups are strongly electron donating and enormously accelerate the rate of spontaneous solvolysis.

Compounds given by Formula 6 are triggered to release a potent bifunctional alkylating agent following activation by tumor associated proteases in a similar fashion as for compounds of Formula 1. However, these compounds possess a detoxification functionality which is activated by enzymes ubiquitous to normal cells. This detoxification functionality is comprised of a masked nucleophile which can be unmasked by spontaneously or by normal cellular enzymes. Normal cellular enzymes will detoxify the drug by cleaving the ester or amide functionalities present. This will expose an intramolecular nucleophile which is favorably positioned to capture and detoxify an aziridinium ion that may form. The nucleophile then reacts via an intramolecular nucleophilic reaction to form a 4, 5, or 6 membered ring with displacement of the leaving group X. The intramolecular consumption of the alkylating agent precludes alkylation of cellular DNA and proteins and serves to detoxify the drug. Although, more then one masked nucleophiles may be part of the drug structure, one is sufficient. Converting a bifunctional alkylating agent to a monofunctional alkylating agent results in a dramatic reduction in toxicity. The net effect is that in tissues with low tumor associated protease activity the drug will be detoxified.

The metabolism of the antineoplastic drugs of Formula 6 will follow divergent pathways in tumors and in normal tissues. The spectrum of toxicity of these compounds will be determined by the ratio of activating to detoxifying activity in a given cell or tissue.

Tumors rich in the tumor protease will rapidly activated the drug and release a highly toxic phosphoramide mustard intermediate. A small amount of the drug will be detoxified. But the major pathway will be toxification leading to tumor cell death.

In normal tissues the major metabolic pathway will be detoxification. Only a small amount or the drug will be activated into a toxin. Normal cells will be largely spared of toxicity while tumor cells will be selectively killed. Tumor selectivity is provided by the ability of tumor associated proteases to cleave the (para or ortho) acylamino or acyloxy group of Formula 1 and trigger release of the toxic phosphoramide mustard analog. Tumor associated proteases are able to cleave a wide variety of ester, amides and oligopeptides. Accordingly, a wide variety of substituents can be employed. The substrate requirements for tumor associated proteases are known or may be obtained by routine methodologies. H. Singh, G. Kalnitsky, (1979) *J.Biol.Chem.* 253:4319. Barrett, A. J., Kirschke, H.; (1981) *Methods in Enzymology;* 80:535 Morita, T; (1977) *J.Biochem.;* 82:1495.; Lottenberg, R.; (1981); *Methods in Enzymology;* 80:341. For example, the following substrates are routinely used to assay the indicated protease:

Cathepsin B:
L-Arginine 4-Methoxy-β-Naphthylamide
Nα-Benzoyl-I-Arginine 4-Methoxy-β-Naphthylamide
Nα-Benzoyl-DL-Arginine β-Naphthylamide
Nα-Benzoyl-Dl-Arginine p-Nitroanilide N-Cbz-Ala-Arg-Arg 4-Methoxy-β-Naphthylamide
Nα-Cbz-Arg-Arg 7-Amido-4-Methylcoumarin
Nα-Cbz-Arg-Arg 4-Methoxy-β-Naphthylamide
N-Cbz-Phe-Arg 7-Amido-4-Methylcoumarin
N-Cbz-Val-Lys-Lys-Arg 4-Methoxy-β-Naphthylamide
N-Succinyl-Ala-Ala-Pro-Phe 7-Amido-4-Methylcoumarin
(where CbZ=carbobenzoxy)
Cathepsin D:
Nα Benzoyl-Arg-Gly-Phe-Phe-Leu 4-Methoxy-β-Naphthylamide
N-t-Boc-Phe-Ala-Ala-p-Nitro-Phe-Phe-Val-Leu 4-Hydroxymethylpyridine Ester
(where t-Boc=t-butoxycarbonyl)
Cathepsin L:
N-Cbz-Phe-Arg 7-Amido-4-Methylcoumarin
Dipeptidyl Peptidase II:
lys-Ala 7-Amido-4-Methylcoumarin
lys-Ala 4-Methoxy-β-Naphthylamide
lys-Ala β-Naphthylamide
lys-Pro-4-Methoxy-β-Naphthylamide
Plasmin:
d-Ala-leu-Lys 7-Amido-4-Methylcoumarin
Ala-Phe-Lys 7-Amido-4-Methylcoumarin
Nα-Benzoyl-Dl-Arginine p-Nitroanilide
N-Benzoyl-Phe-Val-Arg' p-Nitroanilide
N-t-Boc-Glu-Lys-Lys 7-Amido-4-Methylcoumarin
N-t-Boc-Val-Leu-Lys 7-Amido-4-Methylcoumarin
N-Cbz-Ala-Ala-Lys 4-Methoxy β-Methylcoumarin
N-Cbz-Gly-Pro-Arg p-Nitroanilide
Gly-Arg p-Nitroanilide
N-Succinyl-Ala-Phe-Lys 7-Amido-4-Methylcoumarin
N-p-Tosyl-Gly-Pro-Arg 7-Amido-4-Methylcoumarin
N-p-Tosyl-Gly-Pro-Lys p-Nitroanilide
D-Val-Leu-Lys p-Nitroanilide
Urokinose and Tissue Plasminogen Activator:
N-Acetyl-Gly-Lys β-Naphthylamide
Ala-Phe-Lys 7-Amido-4-Methylcoumarin
N-Cbz-Gly-Gly-Arg 7-Amido-4-Methylcoumarin
N-Cbz-Gly-Gly-Arg 4-Methoxy-β-Naphthylamide 1
N-a-Cbz-L-Lysine p-Nitrophenyl Ester
N-Glutaryl-Gly-Arg 7-Amido-4-Methylcoumarin
Gly-Arg p-Nitroanilide.
pGlu-Gly-Arg p-Nitroanilide.
D-Val-Leu-Lys p-Nitroanilide.
(where pGlu=pyroglutamic)
The proteases cleave the terminal ester or amide of the above substrates and liberate an aromatic amino or phenol analog. Specificity is determined by the nature of the amino acid chain (shown above in bold) not by the nature of the liberated phenol or aromatic amine.

Cathepsin B activated antineoplastic drugs of Formula 2 and Formula 7 result if $R6CO_2H$ is selected from the following group:
L-Arginine
Nα-Benzoyl-l-Arginine
Nα-Benzoyl-D-Arginine
N-Cbz-Ala-Arg-Arginine
N-Cbz-Phe-Arginine
N-Cbz-Val-Lys-Lys-Arginine
N-Succinyl-Ala-Ala-Pro-Phenylalanine Cathepsin D activated antineoplastic drugs of Formula 2 and Formula 7 result if $R6CO_2H$ is selected from the following group:
Nα Benzoyl-Arg-Gly-Phe-Phe-Leucine
N-t-Boc-Phe-Ala-Ala-p-Nitro-Phe-Phe-Val-Leucine Cathepsin L activated antineoplastic drugs of Formula 2 and Formula 7 result if $R6CO_2H$ is:
N-Cbz-Phe-Arginine Dipeptidyl Peptidase II activated antineoplastic drugs of Formula 2 and Formula 7 result if R6CO2H is selected from the following group:
lys-Alanine
lys-Proline Plasmin activated antineoplastic drugs of Formula 2 and Formula 7 result if $R6CO_2H$ is selected from the following group:
d-Ala-leu-Lysine
Ala-Phe-Lysine
Nα-Benzoyl-Dl-Arginine
N-Benzoyl-Phe-Val-Arginine
N-t-Boc-Glu-Lys-Lysine
N-t-Boc-Val-Leu-Lysine
N-Cbz-Ala-Ala-Lysine
N-Cbz-Gly-Pro-Arginine
Gly-Arginine
N-Succinyl-Ala-Phe-Lysine
N-p-Tosyl-Gly-Pro-Arginine
N-p-Tosyl-Gly-Pro-Lysine
D-Val-Leu-Lysine Tissue Plasminogen Activator and Urokinose and activated antineoplastic drugs of Formula 2 and Formula 7 result if $R6CO_2H$ is selected from the following group:
N-Acetyl-Gly-Lysine
Ala-Phe-Lysine
N-Cbz-Gly-Gly-Arginine
N-Cbz-Gly-Gly-Arginine
N-a-Cbz-L-Lysine
N-Glutaryl-Gly-Arginine
Gly-Arginine
pGlu-Gly-Arginine
D-Val-Leu-Lysine Collagenase activated antineoplastic drugs of Formula 2 and Formula 7 result if $R6CO_2H$ is: N-Succinyl-Gly-Pro-leu-Gly-Proline. Collagenases are known to cleave the leu-gly bond of substrates of this structure. K. Kojima, H. Kinoshita, T. Kato, T. Nagatsu, K. Takada, S. Sakakibara (1979) *Analytical Biochem.* 100:43.The result is the liberation of a Gly-Pro-dipetide which may be rapidly degraded by X-prolyl-dipeptidyl peptidases to release the toxic phosphoramide mustard analog.

The key requirement for the acyloxy or acylamino group of Formula 1 and Formula 6 is that the group be cleaved by a tumor associated protease. A large numbers of alkyl, and aromatic esters and amides are substrates for proteases and may be employed. It is now a routine matter to prepare a library of oligopeptides with combinations of different amino acids. These combinatorially produced oligopeptides may also serve as a source $R6CO_2H$. Gordon E M Barrett R W Dower W J Fodor S P Gallop M A (1994) *J Med Chem* 37(10):1385.; Gallop M A Barrett R W Dower W J Fodor S P Gordon E M; (1994); *J Med Chem* 37(9):1233. Ostresh J M Husar G M Blondelle S E Dorner B Weber P A Houghten R A (1994) *Proc Natl Acad Sci USA* 91(23):11138–42. A rapid screening method to optimize groups $R6CO_2H$ would comprise of coupling the terminal carboxylic acid of combinatorially produced oligopeptides with a fluorescent indicator group such as 7-Amino-4-Methylcoumarin. Cleavage of the terminal amide by purified tumor protease or by tumor cells in vitro will releases the fluorescent 7-Amino-4-Methylcoumarin which can be quantitated in a high throughput automated robotic microwell spectrofluorometric assay using existing technology. Alternatively, a library of the protease activated antineoplastic drugs made with a combinatorially produced library of $R6CO_2H$ could be screened in vitro for cytotoxicity against normal and malignant cells in a high throughput automated robotic microwell cytotoxic assay using existing technology. Using no more then routine methods one may identify acyloxy or acylamino group for of compounds of Formula 1 and Formula 6 that are cleaved by a tumor associated protease.

One skilled in the arts will recognize other compounds which are activated by the enzymatic activity of tumor associated protease to yield a cytotoxic phosphoramide mustard analog. These are to be considered within the scope of the present invention.

The drugs can be administered orally, parenterally or topically. The preferred route of administration is intravenously. The form in which the drugs are given (e.g., powder, tablet, capsule, solution, emulsion) will depend upon the route by which it is to be administered. The quantity of the drugs to be administered will be determined on an individual basis and will be determined in part on consideration of the individuals size, the severity of the symptoms, and the result sought.

The composition of the present invention can optionally include, in addition to the drug other components. The other components included in a particular composition are determined primarily by the route of administration. For example, a composition to be administered orally in tablet form can include, in addition to the drug, a filler (e.g., lactose), a binder (e.g. carboxy-methyl cellulose, gum arabic, gelatin) a flavoring agent, a coloring agent, and a coating material (e.g., wax, or a plasticizer). A composition to be administered in a liquid form can include the drugs of the present invention, and optionally an emulsifying agent, a carrier (e.g. saline or water), a flavoring agent, and or a coloring agent. A composition to be administered in a topical form may include an emulsifying agent, a solvent, stabilizing agents and a base such as polyethylene glycol.

The drugs may also be used to kill tumor cells in vitro such as in aspirated bone marrow preparations. To kill tumor cells in vitro the tumor cells are contacted with a concentration of drug sufficient to achieve the desired cell killing during the time of exposure to the drug.

General Methods of Drug Synthesis

Compounds of Formula 1 can be synthesized by the reaction of the benzyl alcohol A—OH with a compound of Formula 11:

in an inert solvent such as methylene chloride, chloroform, or diethyl ether in the presence of a base such as triethylamine, or diisopropylethylamine. If A is not soluble in a suitable inert solvent or if A bears nucleophilic groups that could react with compound of Formula 11 then protective groups must be employed. The protective groups are removed after the coupling reaction. Standard protective groups may be employed. Suitable hydroxy protective groups include: trimethylsilyl-; tert-butyldimethylsilyl-; beta-(trimethylsilyl) ethoxymethyl; pixyl and vinyl ethers. Suitable protective groups for amino substituents include T-Boc, P-methoxybenzyloxycarbonyl, and 2-(p-biphenyl)-propyl-oxy-carbonyl. These protective groups can be coupled to (and cleaved) using routine methods. Greene, T. W. in *Protective Groups in Organic Synthesis*, John Wiley and Sons, New York, N.Y.(1981).

Compound given by Formula 11 can be made by the reaction of POCl$_3$ with 1 equivalent of the hydrochloride salt of R1H and 1 equivalent of the hydrochloride salt of R2H in an inert solvent in the presence of 4 equivalents of a base such as triethylamine.

Alternatively, Compounds of Formula 1 may be synthesized by the nucleophilic reaction between A—X where X is a good leaving group such as a halogen or tosyl group and a compound given by Formula 12:

in an inert solvent such as benzene, dimethylsulfoxide, dimethylformamide, or methylene chloride. Wherein R1a and R2a are the analogs of R1 and R2 respectively in which the leaving group X is replaced with a hydroxy group or a protected hydroxy group. After the coupling reaction with A—X the product is treated with an appropriate reagent to convert the group R1a and R2a to R1 and R2 respectively. For example, if the leaving group on R1 and R2 is Chloride then thionyl chloride may be employed.

Compounds of the formulae given by, A—OH, R1, R1a, R2, and R2a are known compounds or may be synthesized by one skilled in the arts of organic chemistry using established synthetic transformations and procedures.

Compounds given by Formula 2 can be synthesized in a similar manner by reacting a compound of Formula 11 or Formula 12 with a compound of Formula 13a or Formula 13b respectively in an inert solvent.

Formula 13a

Formula 13b

Where X is a good leaving group. Compounds given by Formula 13a and 13b are known or may be synthesized by one skilled in the arts of organic chemistry using established synthetic transformations and procedures.

Compounds of the following structure given by Formula 14 are also known or readily synthesized by one skilled in the arts of organic chemistry using known procedures:

Formula 14

If Formula 14 is an oligo peptide then it may be synthesized using conventional techniques of peptide chemistry. Compounds given by Formula 14 may be reacted with the known or easily prepared compounds of Formulae 15a–15b to form the corresponding ester or amide shown as Formula 16a–16b. A wide range of conventional coupling reagents such as dicyclohexylcarbodiimide, carbonyldiimidazole, and bis (2-oxo-3-oxazolidinyl)-phosphonic chloride employed may be employed. Alternatively, the acid chloride of Formula 14 may be prepared by thionyl or oxalyl chloride and reacted with compounds of Formula 15 in the presence of a base such as triethylamine.

Formula 15a

Formula 15b

Formula 16a

Formula 16b

Compounds of Formula 16 can be transformed into compounds of Formula 13b by treatment with reagents such as thionyl chloride, tosyl chloride and base, or phosphorus tribromide.

One skilled in the art of organic chemistry will recognize many other synthetic methodologies to make the compounds encompassed within this disclosure.

EXAMPLES:

The following prototype compound(V-Isophos) was synthesized and its antineoplastic activity examined:

V-Isophos 4-acetoxy 3-methoxy benzyl alcohol was reacted with an excess of Cl—(PO)(NHCH$_2$CH$_2$Cl)$_2$ in anhydrous methylene chloride at room temperature in the presence of 1 equivalent of triethylamine under argon for 24 hours. The product was purified by chromatography on silica. To yield a white crystalline material. The structure was confirmed by proton NMR, phosphorus NMR and high resolution mass spectrometry.

The Cl—(PO)(NHCH$_2$CH$_2$Cl)$_2$ was synthesized by the reaction in methylene chloride of beta chloroethylamine hydrochloride (2 equivalents), phosphorus oxychloride (1 equivalent) and triethylamine (4 equivalents). The base was added slowly dropwise over approximately 4 hours with cooling at −78° C. under argon. After 24 hours the triethylamine hydrochloride was removed by filtration. Then the organic phase was rapidly washed 2x's with ice cold saturated aqueous NaCl. After removing the solvent exvacuo the residue was dryed by co-evaporation X3 with toluene. Upon storage the product crystallized. Proton and phosphorus NMR were consistent with the desired product.

Figure 1:
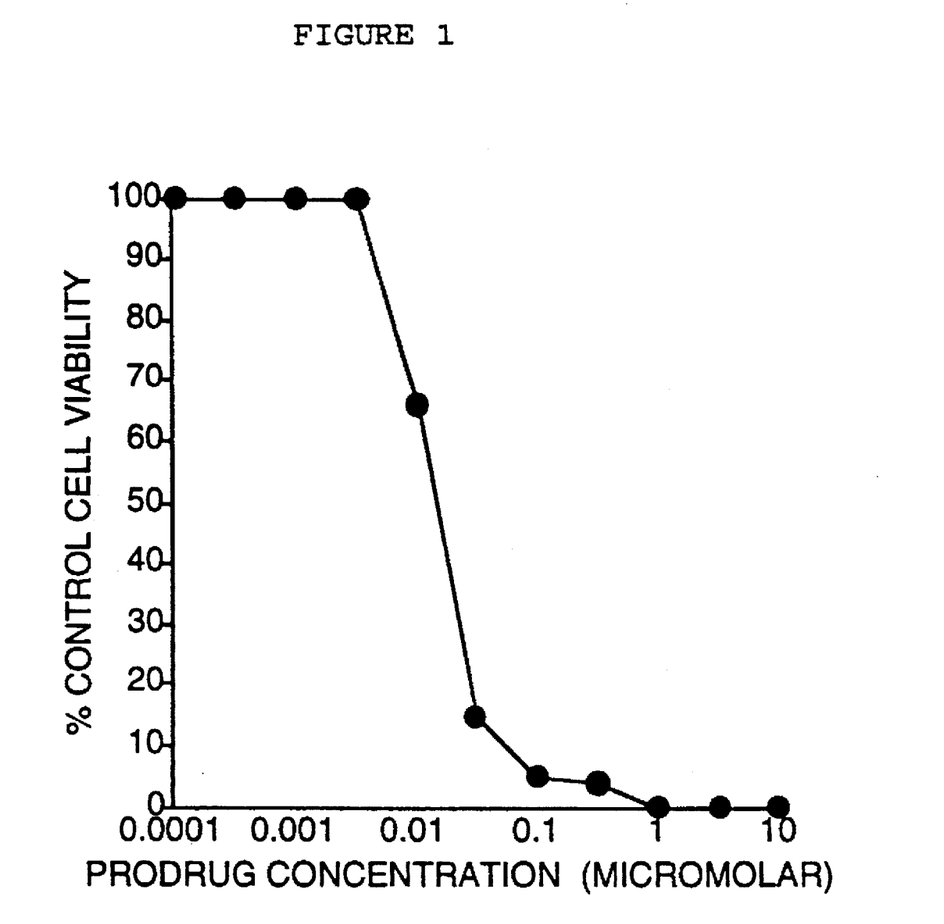
FIG. 1 is a graph of the toxicity of V-Isophos for CEM cells in vitro.

V-Isophos was designed to liberate isophosphoramide mustard upon the unmasking of the p-hydroxy group by esterases or tumor associated proteases with esterase activity. V-Isophos and Isophosphoramide mustard were tested in vitro for cytotoxicity towards GEM cells following a 4 day incubation. After 4 days the percentage of viable cells was measured by employing a standardized assay based upon the conversion of a tetrazolium salt to a formazan chromaphore by viable cells. (T. Mossman; *J. Immunol. Methods* 65:55 (1983)) The production of the chromaphore was measured spectrophotometrically with a Molecular Devices Vmax plate reader at 570 nm. From the optical density data a computer program calculated the drugs cytotoxic effect and concentration that resulted in a 50% reduction in cell viability (IC$_{50}$ value). The data is summarized in FIG. 1. V-Isophos was highly toxic to the CEM cells with an IC$_{50}$ of approximately 0.01 micromolar. In contrast isophosphoramide mustard was nontoxic in this assay at up to 10 micromolar. This in vitro testing was kindly performed by R. Buckheit, Southern Research Institute.

Figure 2:
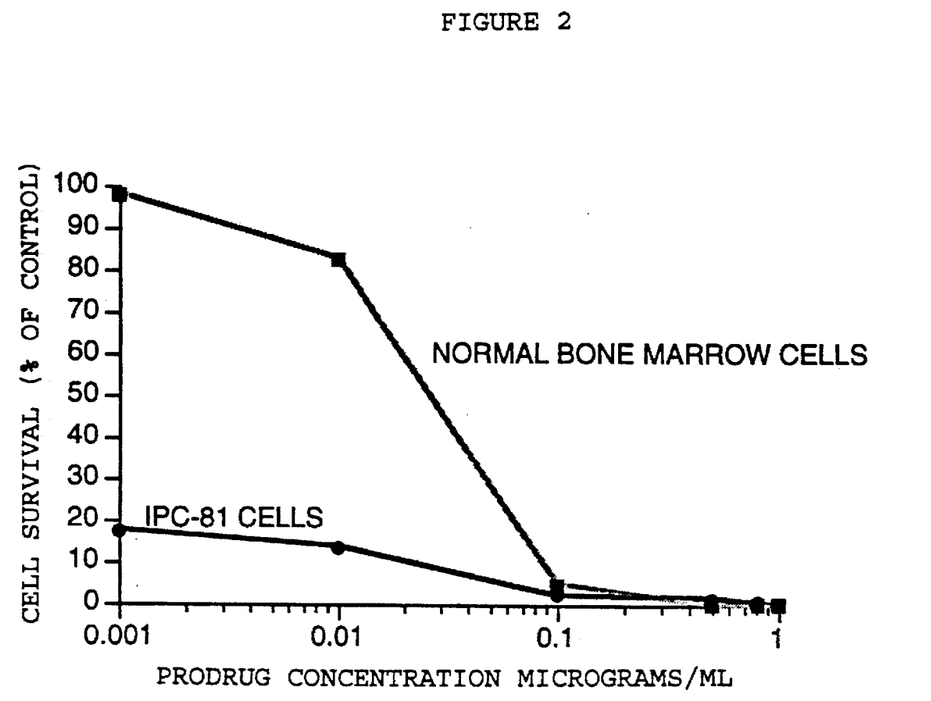
FIG. 2 is a graph of the toxicity of V-Isophos for IPC-81 leukemic cells and normal rat marrow cells in vitro.

V-Isophos was also examine for anticancer activity against IPC-81 rat myeloid leukemic cells and for toxicity against normal rat bone marrow colony forming cells. This in vitro assay was kindly performed by A. Yeager at Johns Hopkins Oncology Center using standardized published procedures. The results demonstrated that V-Isophos had significant activity against the leukemic cells. The results are summarized in FIG. 2.

Figure 3:
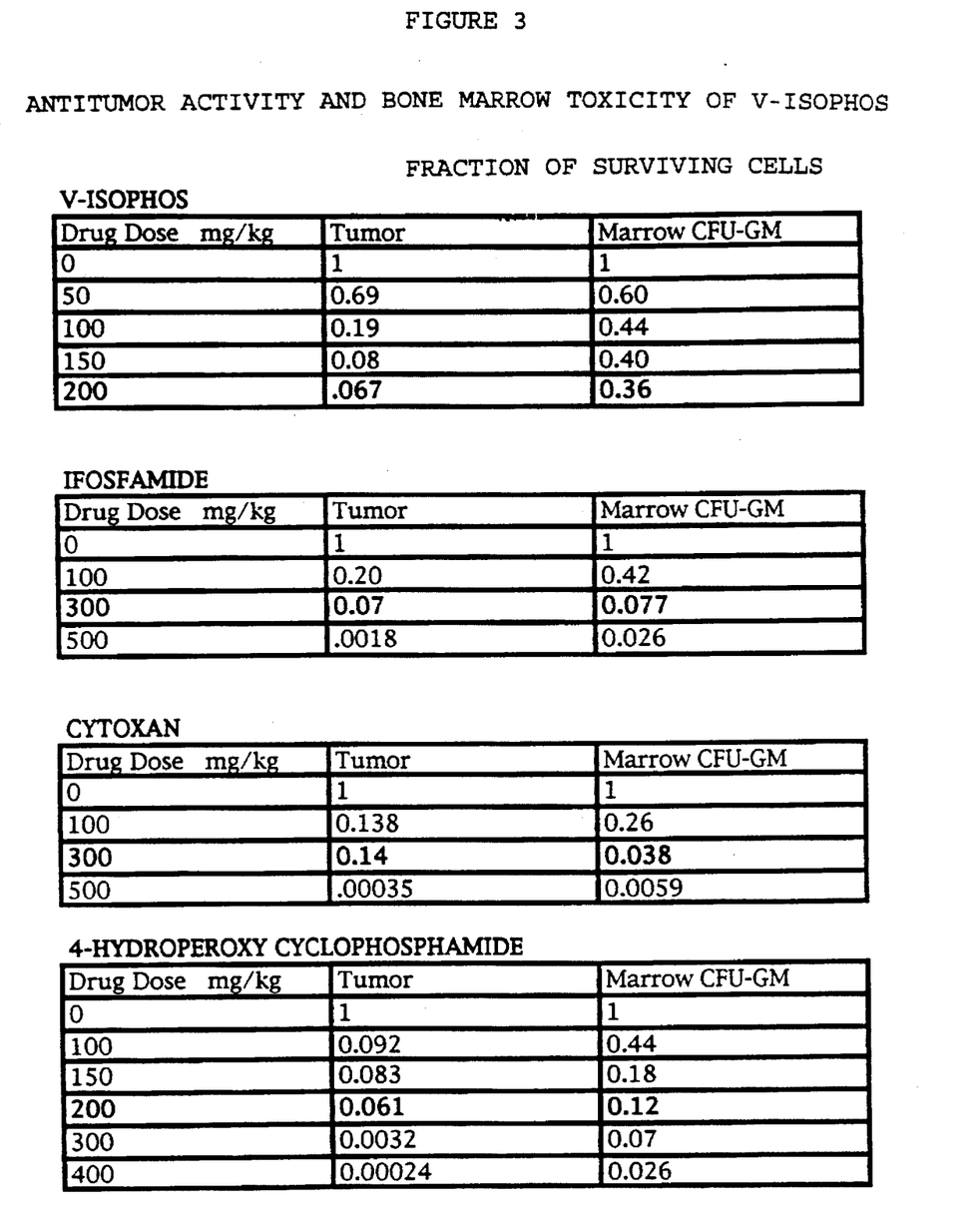
FIG. 3 is a table which details the toxicity of V-Isophos for FSAII fibrosarcoma cells and normal bone marrow cells after administration of the drug to tumor bearing mice. Also shown is data for cytoxan, 4-hydroperoxy-cyclophosphamide, and ifosfamide.

V-isophos was also examined in mice against the FSA2 fibrosarcoma. Mice with established tumors (approximately 100 mg in size in each flank) were given a single IP injection of V-isophos, cytoxan, 4-hydroperoxycydophosphamide or ifosfamide at varying dosages. After 24 hours the mice were sacrificed and the fraction of viable tumor colony forming cells and bone marrow colony forming cells (CFU-GM) were assayed in drug treated and control mice. This screening experiment was kindly conducted by B. Teicher at the Dana Farber Cancer Center and employed standardized published methods. The results are summarized in FIG. 3. V-Isophos was found to be highly active against the tumor and less marrow toxic then the other agents tested.

Equivalents

Those skilled in the arts will recognize or be able to ascertain, using no more than routine experimentation, many equivalents to the specific materials and components described herein. Such equivalents are intended to be encompassed in the scope of the following claims.

I claim:

1. An antineoplastic compound represented by the following structural formula:

wherein:

R1 is a beta-X-ethyl amino group or a beta-X-ethyl amino group substituted on one or more nitrogen or carbon atoms;

X is a good leaving group or a halogen;

R2 is selected from the group consisting of a beta-X-ethyl amino group, a beta-X-ethyl amino group substituted on one or more nitrogen or carbon atoms, an amino group and a substituted amino group; and

A is a benzyloxy derivative with one or more acyloxy or acylamino groups in the para or ortho positions relative to the phosphoester, with the proviso that the acyloxy or acylamino groups are not a substituted or unsubstituted p-guanidino-benzoyloxy group or a p-guanidino-benzoylamino group.

2. An antineoplastic compound of claim 1 of the following structure:

Wherein R3 and R4 is H; an alkyl group; a methyl group; or an ethyl group; —$CH_2$—$CO_2$—Y; or an N substituted methylene-carbonyl-amino group; wherein Y is an alkyl group; a methyl group; or an ethyl group; and R5 is an acyl-oxy group; or an acyl-amino group; and wherein the benzyl ring may optionally be substituted with inert groups; alkyl group; alkyloxy groups, methoxy, or halogens.

3. An antineoplastic compound of claim 2 of the following structure:

4. An antineoplastic compound of claim 3 of the following structure:

$$R_5-\text{phenyl}-\overset{H}{\underset{H}{C}}-O-\overset{O}{\underset{\|}{P}}(-NH-CH_2-CH_2-Cl)(-NH-CH_2-CH_2-Cl)$$

or $$R_5-\text{phenyl}-\overset{H}{\underset{H}{C}}-O-\overset{O}{\underset{\|}{P}}(-N(CH_2-CH_2-Cl)_2)(-NH_2)$$

5. An antineoplastic compound of claim 4 wherein R5 has the following structure:

wherein R6 is a substituted or unsubstituted alkyl or phenyl group; or wherein R6 selected such that R6—COOH is a substituted or unsubstituted amino acid or an oligopeptide comprised of from 2 to about 20 substituted or unsubstituted amino acids.

6. An antineoplastic compound of claim 2 wherein R5 has the following structure:

$$R_6-\overset{O}{\underset{\|}{C}}-\underset{H}{N}- \quad \text{or} \quad R_6-\overset{O}{\underset{\|}{C}}-O-$$

wherein R6 is a substituted or unsubstituted alkyl or phenyl group; or wherein R6 selected such that R6—COOH is a substituted or unsubstituted amino acid or an oligopeptide comprised of from 2 to about 20 substituted or unsubstituted amino acids.

7. An antineoplastic compound of claim 6 wherein:

R1 is a beta-X-ethyl-amino group which bears a masked nucleophile substituent on the nitrogen or carbon atoms such that the substituent is located 3, 4, or 5 atoms from the group X; wherein X is a good leaving group or a halogen; and wherein the nucleophile is a hydroxy group; an amino group; a carboxylate group; or a thiol.

8. An antineoplastic compound of claim 2 wherein R5 has the following structure:

$$R_6-\overset{O}{\underset{\|}{C}}-\underset{H}{N}- \quad \text{or} \quad R_6-\overset{O}{\underset{\|}{C}}-O-$$

wherein R6 is a substituted or unsubstituted alkyl or phenyl group; or wherein R6 selected such that R6—COOH is a substituted or unsubstituted amino acid or an oligopeptide comprised of from 2 to about 20 substituted or unsubstituted amino acids;

R1 is a beta-X-ethyl-amino group which bears a masked nucleophile substituent on the nitrogen or carbon atoms such that the substituent is located 3, 4, or 5 atoms from the group X; wherein X is a good leaving group or a halogen.

9. An antineoplastic compound of claim 8 of the following structures:

$$R_5-\text{phenyl}-\overset{H}{\underset{H}{C}}-O-\overset{O}{\underset{\|}{P}}\begin{pmatrix}-NH-CH_2-CH_2-Cl\\-N-CH_2-CH_2-Cl\\ \phantom{-N}|\\ \phantom{-N}CH_2\\ \phantom{-N}|\\ \phantom{-N}CH_2\\ \phantom{-N}|\\ \phantom{-N}R_7\\ \phantom{-N}|\\ \phantom{-N}C=O\\ \phantom{-N}|\\ \phantom{-N}R_8\end{pmatrix}$$

or $$R_5-\text{phenyl}-\overset{H}{\underset{H}{C}}-O-\overset{O}{\underset{\|}{P}}\begin{pmatrix}-NH-CH_2-CH_2-Cl\\-N-CH-CH_2-Cl\\ \phantom{-N}H \phantom{-}|\\ \phantom{-N}\{CH_2\}_{n=1,2,3}\\ \phantom{-N}|\\ \phantom{-N}R_7\\ \phantom{-N}|\\ \phantom{-N}C=O\\ \phantom{-N}|\\ \phantom{-N}R_8\end{pmatrix}$$

or $$R_5-\text{phenyl}-\overset{H}{\underset{H}{C}}-O-\overset{O}{\underset{\|}{P}}\begin{pmatrix}-NH-CH_2-CH_2-Cl\\-N-CH_2-CH-Cl\\ \phantom{-N}H \phantom{-}|\\ \phantom{-N}\{CH_2\}_{n=2,3,4}\\ \phantom{-N}|\\ \phantom{-N}R_7\\ \phantom{-N}|\\ \phantom{-N}C=O\\ \phantom{-N}|\\ \phantom{-N}R_8\end{pmatrix}$$

or or wherein R7 is O, NH, or S and R8 is an alkyl group, a substituted or unsubstituted phenyl group, or wherein R8—CO₂H is a substituted or unsubstituted amino acid.

10. An antineoplastic compound of claim 1 wherein:
R1 is a beta-X-ethyl-amino group which bears a masked nucleophile substituent on the nitrogen or carbon atoms such that the substituent is located 3, 4, or 5 atoms from the group X; wherein X is a good leaving group or a halogen.

11. An antineoplastic compound of claim 10 wherein:
R2 is a beta-X-ethyl-amino group which may optionally bear substituents on the nitrogen or carbon atoms such that a masked nucleophile is located with 3, 4, or 5 atoms between the nucleophile and the group X; and wherein X is a good leaving group or a halogen.

12. An antineoplastic compound of claim 10 wherein:
X is chlorine; and wherein the nucleophile is a hydroxy group; an amino group; a carboxylate group; or a thiol.

13. An antineoplastic compound of claim 10 wherein the masked nucleophile is an acyloxy group; an acyl-sulfanyl group; or acyl-amino group.

14. An antineoplastic compound of claim 10 which when exposed to a tumor associated protease or esterase is rendered toxic to a cell; wherein the tumor associated protease is selected from the following group consisting of: urokinase; tissue plasminogen activator, Cathepsin B; Cathepsin C; Cathepsin D; plasmin; collagenase; Type IV collagenase; stromelysin; and dipeptidyl peptidase.

15. An antineoplastic compound of claim 1 in which R1 and R2 are —NHCH₂CH₂Cl.

16. An antineoplastic compound of claim 1 in which R1 is —N(CH₂CH₂Cl)₂ and R2 is —NH₂.

17. An antineoplastic compound of claim 1 of the following structure:

18. A method for killing tumor cells comprising contacting the cells in vitro or in vivo with a concentration of a compound of claim 1 high enough to achieve the desired effect.

19. A method of treating tumors in a patient in need thereof comprising administering an effective amount of a compound of claim 1.

20. A method for killing tumor cells comprising contacting the cells in vitro or in vivo with a concentration of a compound of claim 6 high enough to achieve the desired effect.

21. A method of treating tumors in a patient in need thereof comprising administering an effective amount of a compound of claim 6.

22. A method for killing tumor cells comprising contacting the cells in vitro or in vivo with a concentration of a compound of claim 10 high enough to achieve the desired effect.

23. A method of treating tumors in a patient in need thereof comprising administering an effective amount of a compound or claim 10.

24. A method for killing tumor cells comprising contacting the cells in vitro or in vivo with a concentration of a compound of claim 7 high enough to achieve the desired effect.

25. A method of treating tumors in a patient in need thereof comprising administering an effective amount of a compound of claim 7.

* * * * *